United States Patent
Bigner et al.

(10) Patent No.: US 6,503,503 B1
(45) Date of Patent: Jan. 7, 2003

(54) ALLOGENEIC CELLULAR VACCINE

(75) Inventors: Darell D. Bigner, Mebane, NC (US);
John H. Sampson, Durham, NC (US);
David M. Ashley, Victoria (AU);
Laura P. Hale, Hillsborough, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/855,280

(22) Filed: May 13, 1997

(51) Int. Cl.[7] .................. A61K 48/00; C12N 15/87; C12N 5/02; C12N 15/63
(52) U.S. Cl. .................. 424/93.21; 424/93.2; 424/93.1; 435/325; 435/320.1; 435/455
(58) Field of Search .................. 424/93.21, 93.1, 424/93.2; 435/325, 455, 320.1

(56) References Cited

U.S. PATENT DOCUMENTS 5,674,486 A * 10/1997 Sobol et al. ............. 424/93.21
5,705,151 A *  1/1998 Dow et al. ............... 424/93.21
6,187,307 B1 *  2/2001 Cohen .................... 424/93.21

OTHER PUBLICATIONS

Pardoll (1993) Immunology Today; 14(6), 310–316.*
Dranoff et al. (1993) Proc. Natl. Sci. Acad. USA; 90, 3539–3543.*
Vieweg et al. (1995) Cancer Investigation; 13(2), 193–201.*
Fox (1994) Bio/Technology; 12,128.*
Kim et al. (1992) Int. J. Cancer; 51, 283–289.*
Zhai et al. (1996) J. Immunol.; 156, 700–710.*
Moscatello et al. (1996) Oncogene; 13, 85–96.*
Flexnor et al. (1988) Nature; 335, 259–262.*
Toes et al., "Protective Antitumore Immunity Induced by Immunization with Completely Allogeneic Tumor Cells", Cancer Research vol. 56 pp. 3782–3787, Aug. 15, 1996.

* cited by examiner

Primary Examiner—Anne Marie S. Wehbé
(74) Attorney, Agent, or Firm—Banner & Witcoff, Ltd.

(57) ABSTRACT

Vaccination with an allogeneic cell line modified with genetic material encoding specific protein antigens is an effective technique for the delivery of protein antigens to the host's antigen presentation system. The immune response generated by this vaccine is restricted by the major histocompatibility complex type of the host and not the vaccinating cell line. This immunization strategy may be used to treat or prevent tumors or infectious diseases of a mammal.

13 Claims, 7 Drawing Sheets

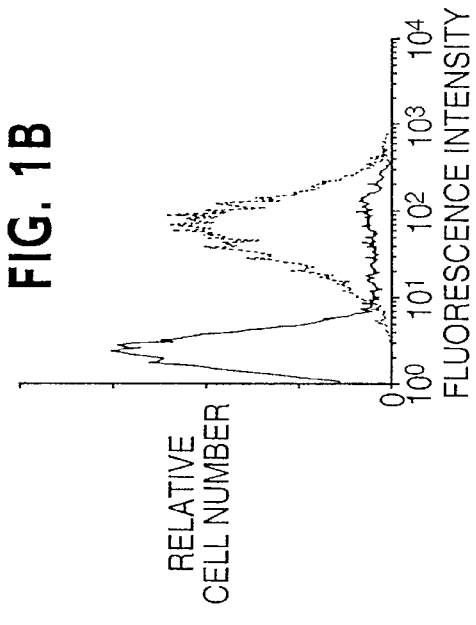
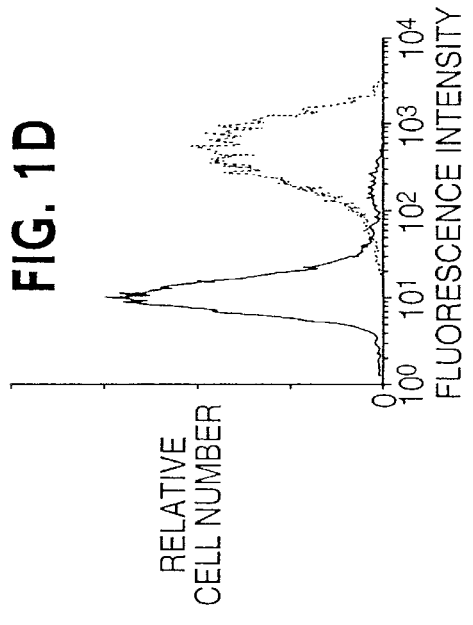
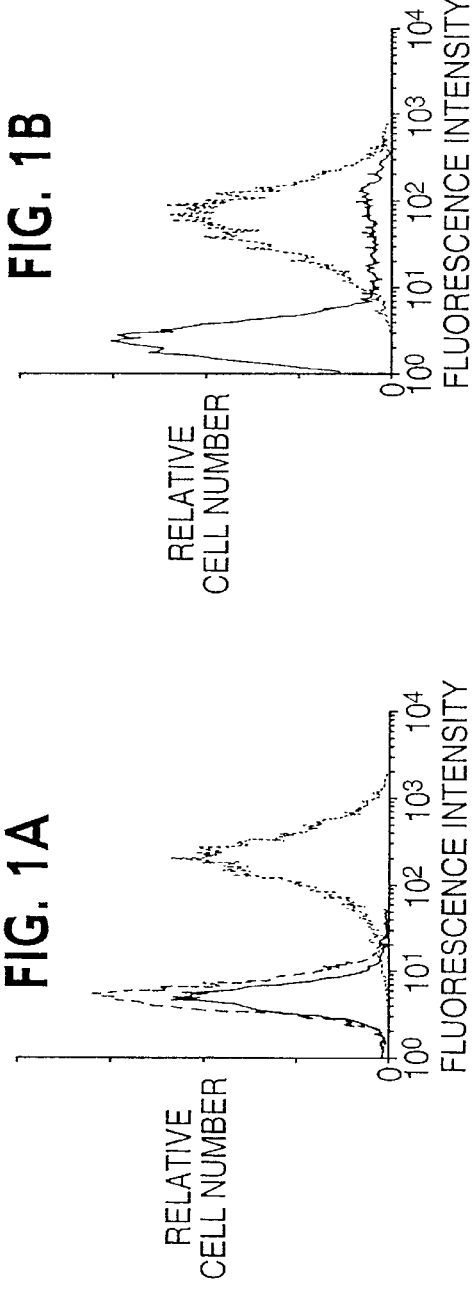
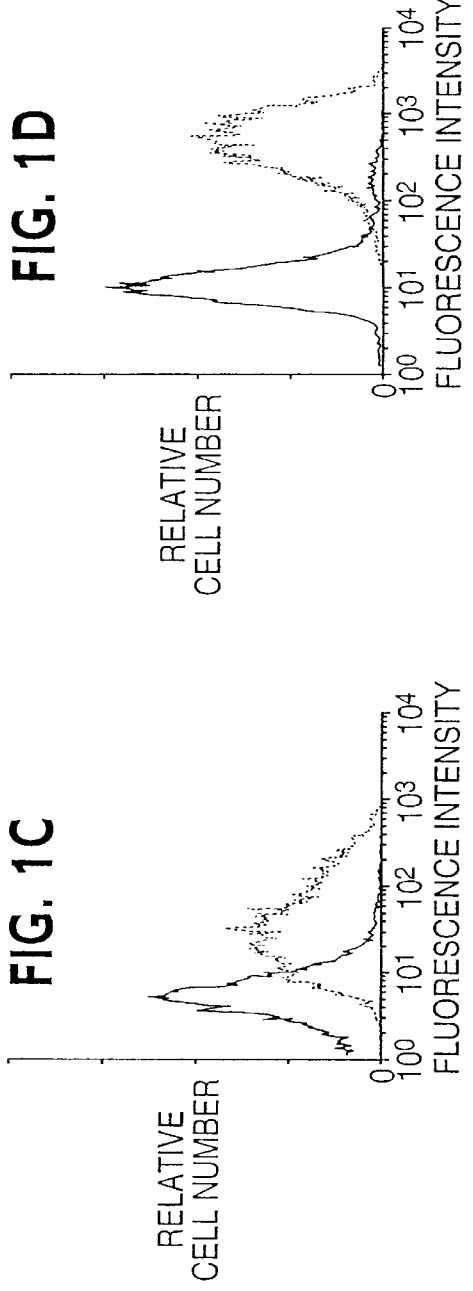

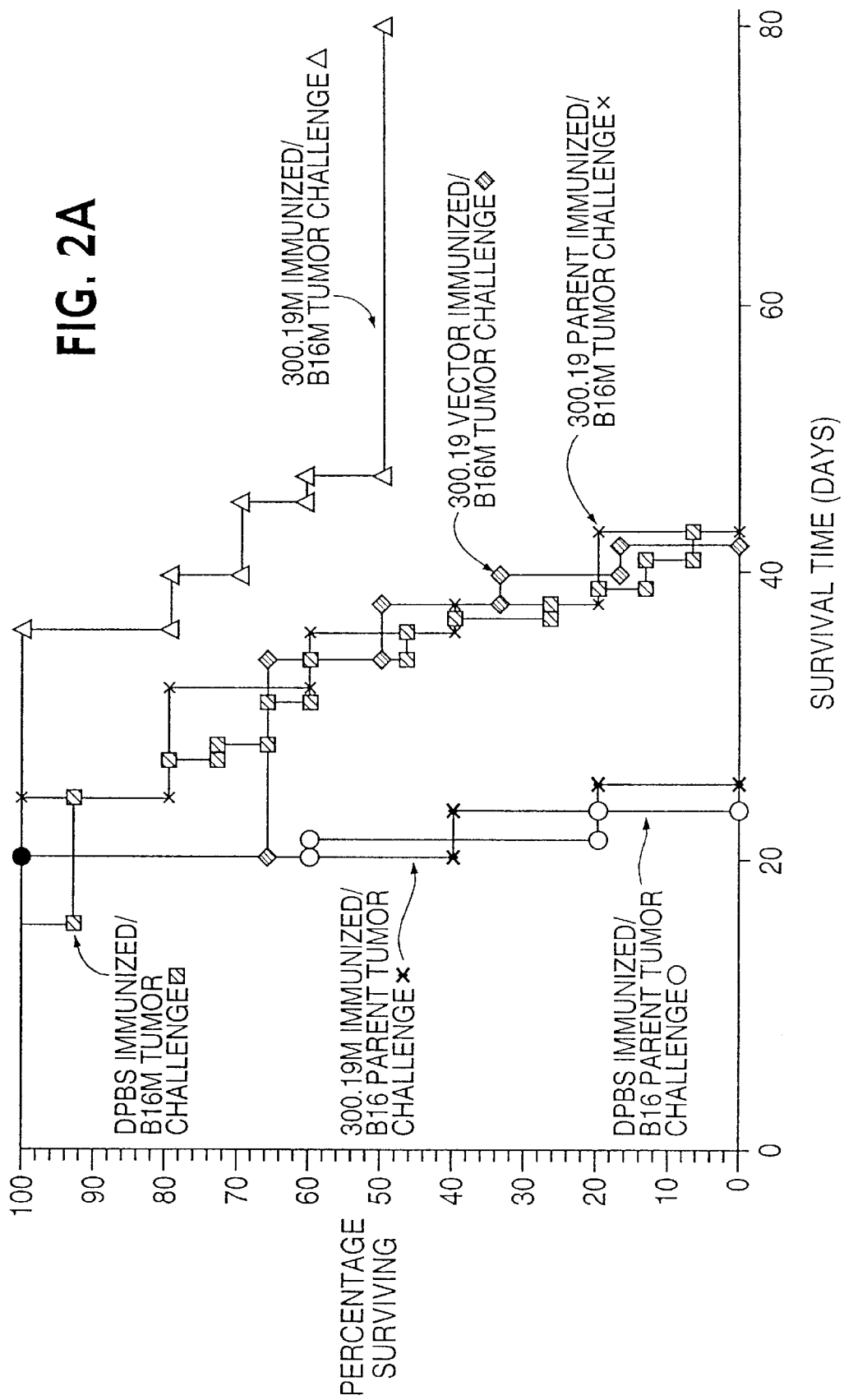

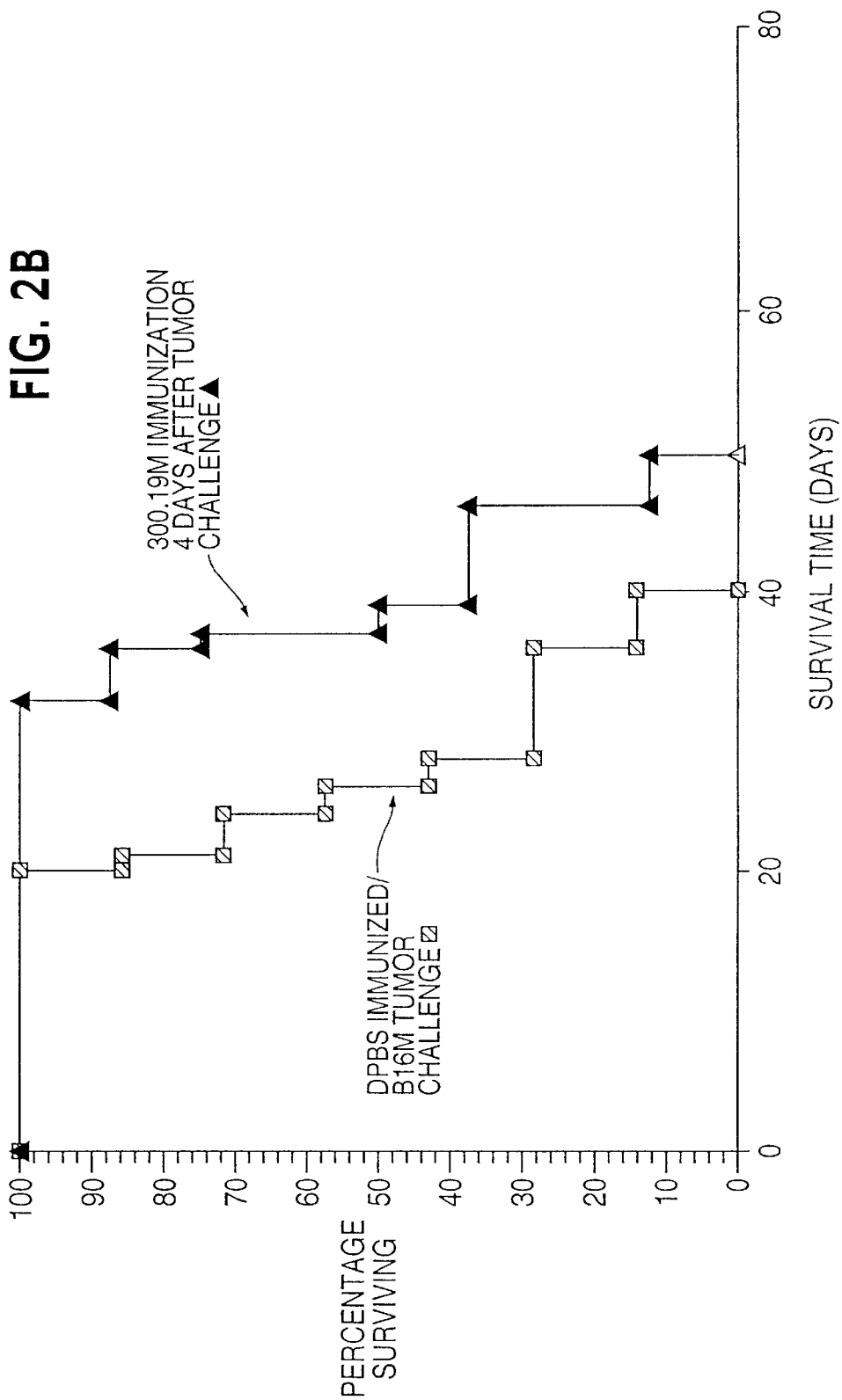

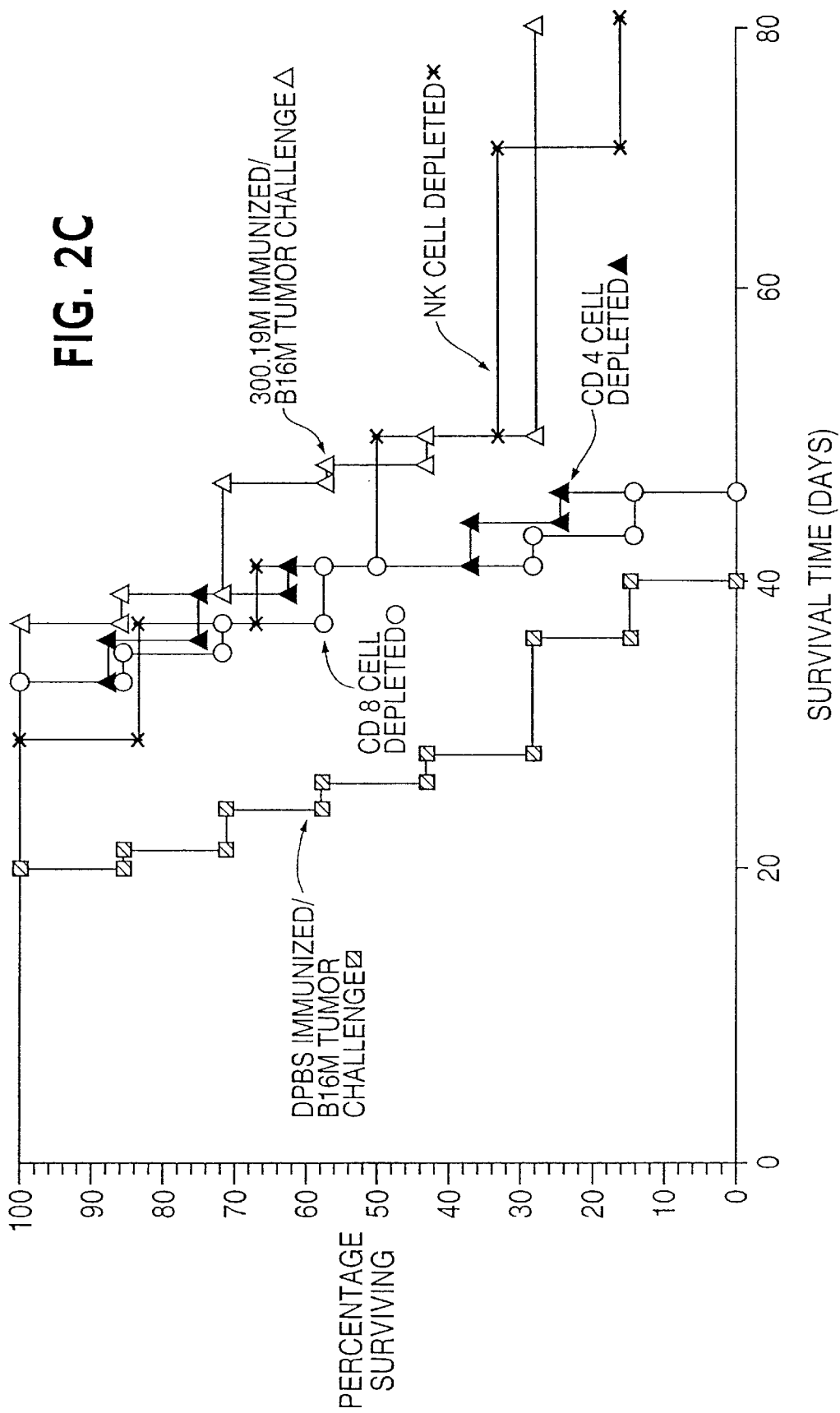

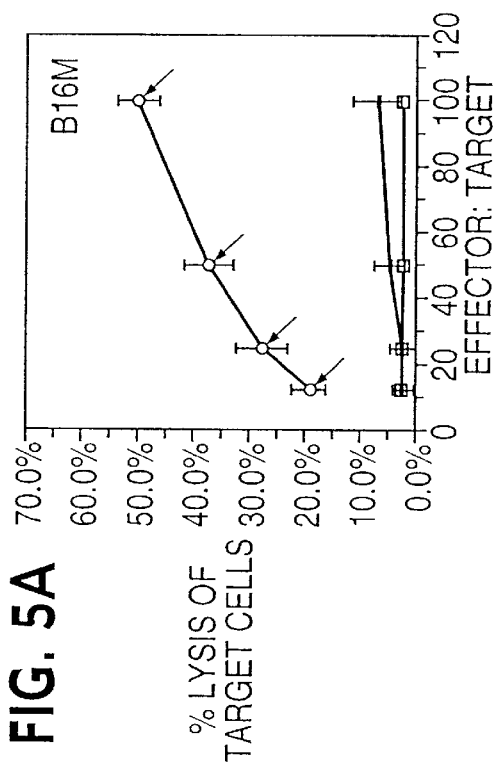
FIG. 5A
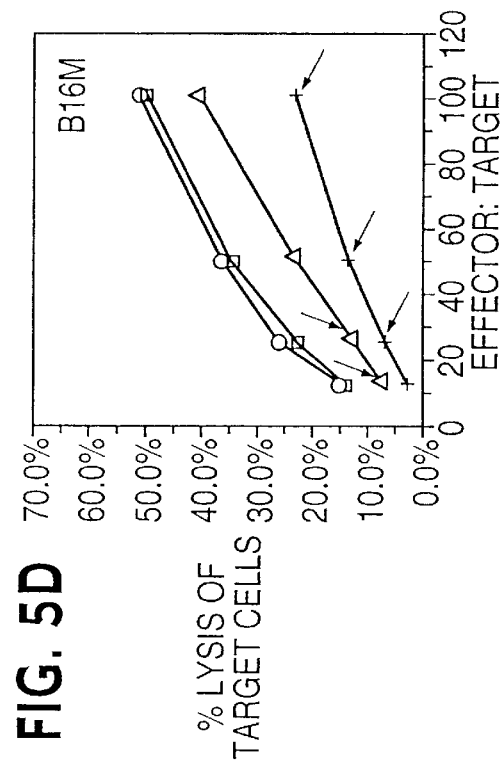
FIG. 5B
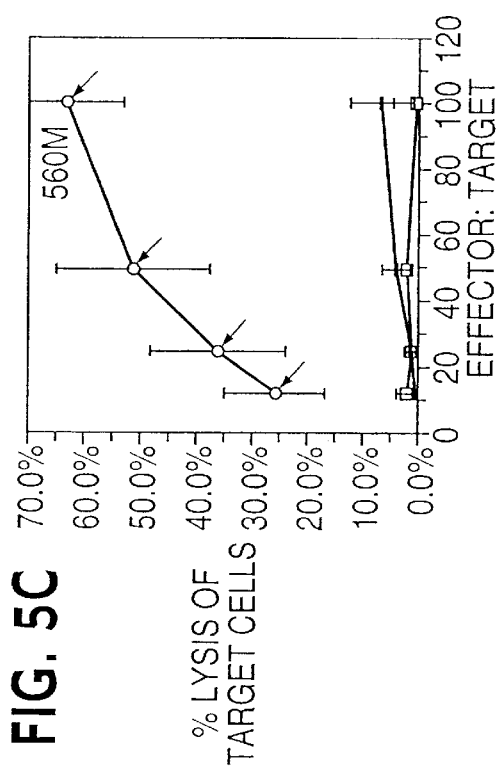
FIG. 5C
FIG. 5D

ALLOGENEIC CELLULAR VACCINE

The U.S. Government has a paid-up license in this invention and the right in limited circumstances to require the patent owner to license others on reasonable terms as provided for by the terms of 5 R37-CA-11898-26 and 5 P50-NS-20023-13 awarded by the National Institutes of Health.

TECHNICAL AREA OF THE INVENTION

The invention relates to the area of allogeneic cellular vaccines. More particularly, the invention relates to the use of allogeneic cellular vaccines for the prevention and treatment of tumors, especially of the central nervous system. The invention also relates to the prevention and treatment of infectious diseases.

BACKGROUND OF THE INVENTION

Brain tumors have historically proved resistant to cell mediated immunotherapies. Previously, it had been postulated that the brain is an immunologically privileged site based upon studies in which tumors transplanted into the brains of outbred rats were often successfully established, whereas the same tumors transplanted subcutaneously were frequently rejected (Shirai 1921; Murphy and Sturm 1923). Further studies demonstrated that histoincompatible skin grafts, which were vigorously rejected when applied orthotopically, grew successfully when implanted within the brain away from the ventricular system (Medawar 1948). The concept of immunologic privilege within the brain has also been supported clinically by the failure of tumors metastatic to the central nervous system (CNS) to respond to immunotherapy protocols that were successful systemically (Grooms et al. 1977; Mitchell 1989). In contrast, inflammatory cells have been observed to regularly infiltrate gliomas (Ridley and Cavanagh 1971; Takeuchi and Barnard 1976; Wood and Morantz 1979). Recent studies have demonstrated that primary subcutaneous tumor transplants can confer resistance to subsequent intracerebral tumor challenge (Scheinberg et al. 1963; Scheinberg et al. 1965; Fakhrai et al. 1996; Sampson et al. 1996). Thus, the more contemporary hypothesis is that the immune privilege of the brain is only partial, particularly with respect to brain tumors. That is, brain tumors express antigens that are potentially immunogenic, but the host's immune system is unable to mediate tumor rejection.

Recently, a number of groups have transfected genes encoding a variety of proteins into brain tumor cells in an attempt to overcome the relative lack of immune response to brain tumors. Genes encoding a variety of cytokines, such as γ-interferon (Watanabe et al. 1989; Mizuno et al. 1994), TNF-α (Takaoka et al. 1994), and IL-7 (Aoki et al. 1992) have been transfected into brain tumor cells and have led to reduced tumor cell growth in animal models. Several investigators have cotransplanted tumor cells with cytokine-secreting cells. Co-transplantation of IL-4-secreting LT-1 plasmacytoma cells with the U87 MG human glioma line intracerbrally in athymic mice resulted in prolonged survival compared with U87 MG alone (Yu et al. 1993). Co-implantation of IL-2 and IFN-γ producing allogeneic fibroblasts with G1261 glioma (Glick et al. 1995) resulted in increased survival as compared to G1261 alone. Co-implantation of RG-2 glioma cells and retrovirally infected cell lines producing IL-2 or IFN-γ generated a cell-mediated anti-tumor response. However, this response was short-lived, and animals suffered severe toxicity, including vasogenic brain edema and early demise (Tjuvajev et al. 1995).

There have now been several reports of successful active immunotherapy in rodent brain tumor models using intradermal vaccines. Fakhrai et al. have reported the effects of a vaccination strategy employing a TGF-β antisense methodology in eradicating the 9L gliosarcoma from the CNS (Fakhrai et al. 1996). More recently, we have reported that subcutaneous vaccination with irradiated B16-F10 murine melanoma cells, genetically engineered to produce GM-CSF, IL-3, or IL-6, stimulated a potent and persistent response to intracerebral B16–F10 tumors and offered protection against CNS tumor challenge. Subcutaneous vaccination with irradiated B16–F10 cells producing GM-CSF also increased the survival of CNS tumor-bearing mice (Sampson et al. 1996).

A major limitation to all of these approaches is the reliability of obtaining and growing tumor cells from a high percentage of fresh tumor samples without contamination by normal tissue (Dillman et al. 1993; Logan et al. 1993). The use of autologous CNS tissue for the generation of vaccines also carries the hypothetical risk of causing an experimental allergic encephalitis-like illness if cross-reactive antigens are present in the vaccine and tolerance is broken (Strauss et al. 1982; Dal Canto et al. 1995; Swanborg 1995).

Thus, there is a need in the art for renewable, safe, cost-effective therapeutic methods for delivering antigens specific to tumors or infectious agents to the immune system of a mammal.

SUMMARY OF THE INVENTION

It is an object of the invention to provide a method of immunizing a mammal against an antigen.

It is another object of the invention to provide a method of immunizing a mammal against two or more antigens.

It is a further object of the invention to provide a method of immunizing a mammal against a disease-specific antigen.

These and other objects of the invention are provided by one or more of the embodiments described below. One embodiment of the invention provides a method of immunizing a mammal against an antigen. The mammal is immunized with an allogeneic cell which has been transfected with a recombinant nucleic acid molecule which encodes the antigen. The transfected cell expresses the antigen.

Another embodiment of the invention provides a method of immunizing a mammal against an antigen. The mammal is immunized with at least two allogeneic cells. A first allogeneic cell has been transfected with a recombinant nucleic acid molecule which encodes an antigen. The first transfected cell expresses the antigen. The second allogeneic cell has been transfected with a recombinant nucleic acid molecule which encodes a cytokine. The second transfected cell expresses the cytokine.

A further embodiment of the invention provides a method of immunizing a mammal against two or more antigens comprising the step of immunizing the mammal with an allogeneic cell which has been transfected with a recombinant nucleic acid. The nucleic acid comprises two or more open reading frames, each of which encodes an antigen. The transfected cell expresses each of the antigens.

Another embodiment of the invention provides a method of immunizing a mammal against a disease-specific antigen. The presence of a disease-specific antigen in a mammal is determined. The mammal is then immunized with an allogeneic cell which has been transfected with a recombinant nucleic acid molecule which encodes the disease-specific antigen. The allogeneic cell expresses the disease-specific antigen.

The present invention provides the art with allogeneic cellular vaccines which can induce potent CTL responses against an antigen. The invention can be used, inter alia, to prevent or treat a tumor or a disease caused by an infectious agent in a mammal.

BRIEF DESCRIPTION OF THE DRAWINGS

FIG. 1.(A–D) The reactivities of transfected cell lines with the MAb L8A4, which reacts with EGFRvIII and not wild type EGFR. In FIG. 1A, the B16F10 melanoma murine cell line was transfected with plasmid pHbAPr-1-neo containing vector only (B 16V ——), or cDNA encoding EGFRvIII(M -----). In FIG. 1B, the 300.19 pre-B murine cell line was transfected with plasmid pHbAPr-1-neo containing vector only (B16 V ——), or cDNA encoding EGFRvIII (M -----). In FIG. 1C, the 560 astrocytoma murine cell line was transfected with plasmid pHbAPr-1-neo containing vector only (B16 V ——), or cDNA encoding EGFRvIII (M -----). In FIG. 1D, the NR6 fibroblast/3T3 murine cell line was transfected with plasmid pHbAPr-1-neo containing vector only (B16 V ——), or cDNA encoding EGFRvIII (M -----).

FIG. 2.(A–C) Survival data for C57BL/6J mice given 300.19M subcutaneous immunizations. In FIG. 2A, mice were immunized with DPBS 500 $\mu$l SC, or 300.19, or 300.19M cells and then challenged in the brain one week later with either 200 untransfected B16 or the EGFRvIII transfected B16M cells. Immunizations with DPBS (○) and 300.19M (*) did not protect against challenge with parental B16 cells, with all animals succumbing to tumor. Similarly, immunization with either DPBS alone (□), 300.19 parental cells (X), or 300.19V cells (♦) did not protect against challenge with transfected B16M cells, with all animals succumbing to tumor challenge. Vaccination of animals with 300.19M cells (Δ) led to a significant improvement in median survival after subsequent challenge in the brain with B16M cells when compared to any group. In addition, 5 animals (50%) in this group were alive with no evidence of tumor when the experiment was terminated at 80 days.

In FIG. 2B, mice were challenged in the brain with 200 EGFRvIII transfected cells and then immunized four days later with DPBS 0.5 cc SQ (□), or 300.19M cells (▲) 300.19M immunized animals showed significantly longer median survivals.

In FIG. 2C, mice were immunized with 300.19M cells using the same protocol. Twelve days later mice were depleted of either CD8 (○), CD4 (▲), or NK (*) cells by in vivo administration of antibody or left with a complete T cell repertoire (Δ). After depletion, mice were challenged with intracrebral B16M cells. DPBS immunized mice were also challenged as a control (□). CD4 and CD8 cell depleted animals showed significantly worse survival than animals left with a complete T cell repertoire.

FIG. 3.(A–B) Sparse inflammatory infiltrate observed with immunoperoxidase staining and hematoxyline counterstaining in CNS tumors from 300.19M vaccinated animals. The infitrating lymphocyte population consisted of almost entirely T cells, with CD8+ cells more frequently observed than CD4+ cells.

FIG. 4.(A–C) Induction of EGFRvIII specific lytic activity by immunization with 300.19M cells. C57BL/6J mice were immunized with DPBS 0.5 cc SQ (□), 300.19 (†), or 300.19M (○) cells as described. Seven days later, splenocytes were isolated and restimulated for 5 days with B16M cells.

FIG. 5.(A–D) EGFR specific lytic activity elicited by immunization with 300.19M cells is MHC restricted. Splenocytes were isolated from C57BL/6J (H-2 $^b$) 7 days after immunization with DPBS(□),300.19(†),or 300.19M(○) cells as described, then restimulated in vitro with B16M cells for 5 days. In FIG. 5A, cytotoxic activity was measured against B16M (H-2 $^b$) cells. In FIG. 5B, cytotoxic activity was measured against NR6M (H-$2^b$) cells. In FIG. 5C, cytotoxic activity was measured against 560M (H-$2^b$) cells. Only targets with H-$2^b$ MHC type were susceptible to lysis. FIG. 5D shows the role of lymphocyte subsets of EGFR specific lytic activity. Cytotoxic activity of splenocytes from 300.19M immunized C57BL/6J mice against B16M cells was measured in the absence of antibody (□) or with blockade performed by adding purified CD4 (GK1.5) (○), CD8 (2.43) (†) or anti-NK (anti-sialo GM) (Δ) antibodies to individual microwells at the start of the chromium release assay. Error bars have been removed for clarity. It was demonstrated that CD8+ cells were the predominant effectors of in vitro lysis with NK cells also contributing.

DETAILED DESCRIPTION OF THE PREFERRED EMBODIMENTS

Figure 3A:
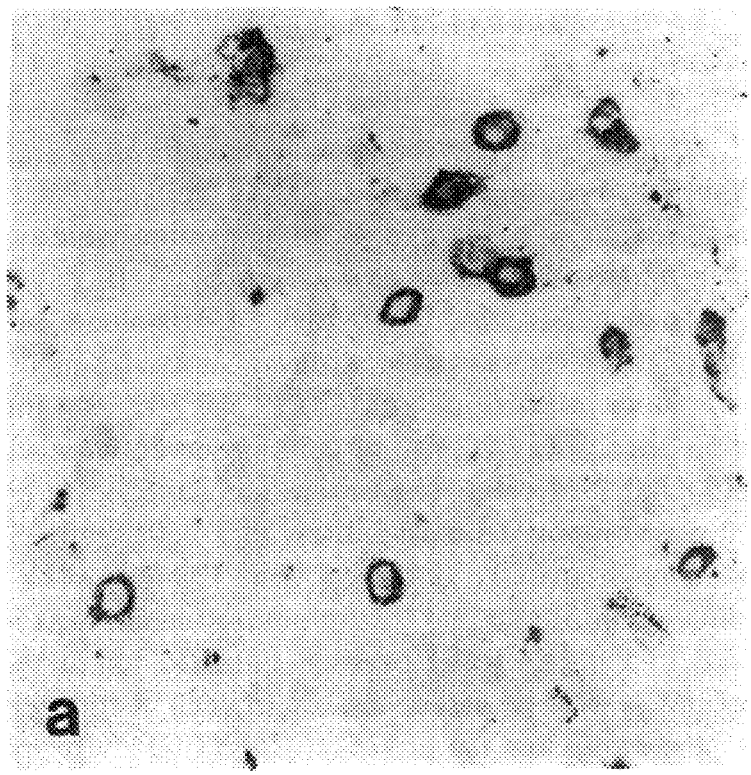
FIG. 3A shows CD8+ cells.

It is a discovery of the present invention that an allogeneic cellular vaccine can induce potent cytotoxic T lymphocyte responses against an antigen expressed by the allogeneic cell. Immunization of mammals with an allogeneic cell transfected to express an antigen leads to the induction of an MHC class I restricted immune response by CD8$^+$ T cells specific for the antigen. Furthermore, such immunization successfully confers protective immunity against challenge with a tumor or infectious agent expressing the antigen. Allogeneic cells transfected with a tumor associated antigen and administered as a vaccine result in the generation of significant, specific, and MHC class I-restricted cytotoxic immune responses against that antigen which are protective against tumor challenge, even in the "immunologically privileged" brain.

Allogeneic cellular vaccine, as used herein, is a preparation which contains an allogeneic cell which expresses a specific antigen and has the ability to induce cytotoxic T lymphocytes directed against the antigen. Vaccination, as used herein, refers to the step of administering the allogeneic cellular vaccine to a mammal to induce such an immune response.

Mammals, including humans and other primates, ungulates, rodents, felines, and canines, can be immunized against an antigen by immunizing the mammal with an allogeneic cell which has been transfected with a recombinant nucleic acid molecule which encodes the antigen. The allogeneic cell typically expresses the antigen. The antigen may be any antigen against which the mammal is capable of mounting an immune response. These antigens include but are not limited to tumor-specific protein antigens and antigens expressed by infectious agents. The method of the invention may be used to immunize the mammal against any type of tumor which occurs in a mammal, including but not limited to melanomas, squamous cell carcinomas, adenocarcinomas, hepatocellular carcinomas, renal cell carcinomas, sarcomas, myosarcomas, leukemias, lymphomas, central nervous system tumors such as gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, Schwannomas, primary and secondary lymphomas, malformative tumors, and metastatic tumors, and tumors of mixed origin, such as Wilms' tumor and teratocarcinomas. Any tumor-specific antigen expressed by the tumor cells, such as the melanoma-specific MAGE and CDK4 antigens, EGFRvIII, p21, Ras, and antigens which are components of central nervous system tumors, such as transferrin receptors and the oncofetal brain tumor antigen HGR-Ag can be used in the method.

Although the antigen targeted in the examples described below was a tumor-specific oncoprotein, any antigen could be targeted using this method. For example, the method of the invention may be used to immunize the mammal against antigens expressed by any type of agent which can infect a mammal, such as bacteria, mycoplasmas, protozoans, viruses, and fungi. The method of the invention is especially suitable for immunization against antigens expressed by latent infectious agents, such as *Mycobacteriwn tuberculosis,* herpes viruses, adenoviruses, papilloma viruses, swine influenza virus, HIV-1, and HIV-2, and for immunization against chronic central nervous system diseases, such as subacute sclerosing panencephalitis, progressive encephalitis, kuru, Creutzfeldt-Jakob disease, bovine spongiform encephalitis, scrapie, and progressive multifocal leukoencephalopathy. Suitable antigens include, for example, herpes simplex virus type 1 glycoproteins B, D, and L; the herpes simplex virus-encoded neurovirulence-associated protein ICP34.5; herpes simplex virus type 2 AG-4 early antigen; HIV envelope glycoproteins gp20 and gp41 and the p24 core antigen; adenovirus E1a, E1b, E2. E3 antigens; bovine papilloma virus protein E1; human papilloma virus tumor antigens E6 and E7; genus-specific papilloma virus antigens such as capsid-specific protein antigens; *Mycobacterium tuberculosis* antigens AG38, Ag85, and the 19 kDa lipoprotein antigen; the hemagglutinin and neuraminidase antigens from swine influenza virus; and measles encephalomyelitis viral antigens.

The allogeneic cell may be any cell from another mammal of the same species as the mammal which is being immunized. Both cell lines and cells freshly isolated from allogeneic tissue may be used, such as fibroblasts, blood, spleen, and bone marrow cells.

Recombinant nucleic acids encoding antigens may be isolated and purified free from other nucleotide sequences by ordinary purification techniques, e.g., using restriction enzymes to isolate desired fragments. The nucleic acid may also be synthesized in vitro, using standard methodology. A recombinant nucleic acid according to the invention includes nucleic acid molecules comprised of DNA or RNA, including coding and regulatory sequences, as well as vector sequences. Recombinant nucleic acids are molecules which are not found in nature. They have been engineered to join together originally separate sequences, usually from different chromosomes or organisms.

Any of the techniques which are available in the art may be used to introduce the recombinant nucleic acid encoding the desired antigen into the allogeneic cell. These techniques are collectively referred to as transfection herein and include, but are not limited to, transfection with naked or encapsulated nucleic acids, cellular fusion, protoplast fusion, viral infection, cellular endocytosis of calcium-nucleic acid microprecipitates, fusion with liposomes containing nucleic acids, and electroporation. Choice of suitable vectors for expression is well within the skill of the art. Antigen expression may be determined by any of a variety of methods known in the art, such as immunocytochemistry, ELISA, Western blotting, radioimmunoassay, or protein fingerprinting.

A mammal may be immunized with one or more antigens. Any tumor- or infectious agent-specific antigen may be used. Open reading frames encoding the antigens may be located on different nucleic acid molecules or may be linked on the same molecule. If multiple nucleic acid molecules are used they may be transfected into the allogeneic cell simultaneously or sequentially, using any of the methods suitable for the transfection of a single nucleic acid. Co-transfection of multiple nucleic acid molecules may be used, inter alia, to take advantage of previously prepared constructs or to limit the size of each recombinant nucleic acid to be transfected. Multiple transfected cells can be used which have been transfected with different antigen-encoding nucleic acids.

The allogeneic cell may also be transfected with a recombinant nucleic acid molecule which encodes a cytokine. Suitable cytokines include, but are not limited to, colony stimulating factors such as granulocyte colony stimulating factor, macrophage colony stimulating factor, and granulocyte-macrophage colony stimulating factor, transforming growth factor-β, chemotactic factors such as gro-alpha and MCP, tumor necrosis factor-α, lymphotoxin, Th2 cytokines such as interferon-γ and interferons-1 through 10, any of the interleukins, leukemia inhibitory factor, and hematopoietic growth factors such as erythropoietin.

According to one embodiment of the invention the presence of a disease-specific antigen is first determined in a mammal, so that an appropriate vaccine can be specifically tailored for the mammal. The presence of a disease-specific antigen in a mammal may be determined by detecting the antigen itself or the nucleic acid encoding it. Any suitable method known to the art may be used to detect the antigen itself, including immunocytochemistry, ELISA, Western blotting, radioimmunoassay, or protein fingerprinting. The nucleic acid encoding the antigen may be detected, inter alia, by Southern blotting, Northern blotting, S1 nuclease digestion, nucleic acid fingerprinting, or nucleic acid sequencing.

The allogeneic cell may be administered subcutaneously, intradermally, intratracheally, intranasally, or intravenously. The cells may be suspended in any pharmaceutically acceptable carrier, such as saline or phosphate-buffered saline. The preferred subcutaneous injection volume is between 50 $\mu$l and 5 ml, containing $10^5$ to $10^9$ allogeneic cells; however, other injection volumes and cell concentrations may be used, depending for example on cell titer, route of administration, size of the mammal being immunized. One skilled in the art can easily make these modifications to injection volume and cell concentration as required for the particular allogeneic cell type and route of administration being used and the particular mammal being immunized. The method contemplates both single and multiple immunizations.

Vaccines comprising allogeneic cells are particularly useful for a variety of reasons. In the case of tumors, the need to obtain large amounts of autologous tumor for the generation of autologous cellular vaccines is a major obstacle in the implementation of clinical studies and in the subsequent treatment of patients. The unlimited supply of candidate cell lines for allogeneic vaccines makes an allogenic cell-based vaccine a simpler, less expensive, and more universally applicable active immunotherapeutic strategy. Allogeneic cell-based vaccines can also help reduce the risks of conditions such as experimental allergic encephalitis and other auto-immune complications (Strauss et al. 1982; Dal Canto et al. 1995; Swanborg 1995). Previous tumor vaccines provided no mechanism to ensure that the response to normal antigens present on the vaccinating cell would not also be enhanced and lead to an autoimmune disease. In fact, there is ample evidence that autoimmune responses frequently occur using these vaccines. Such reactions may be tolerable when directed against non-essential tissues such as the prostate or the breast, but would be devastating if directed against lung or brain tissue. In contrast, our vaccine strategy uses genetic manipulation to drive preferential expression of a specific peptide antigen, thus directing the immune response to this antigen and away from normally expressed antigens that may trigger autoimmune disease. In addition, it employs cells from nonessential tissues that are irrelevant to the host, thus further reducing the risk of induction of autoimmune disease. Obviously, the avoidance of autoimmune responses is paramount in the immunotherapy of both neoplastic and infectious diseases primarily located in essential tissues and especially the brain. Such an approach also allows the application of immunotherapy to a wider range of patients, including those with no tissue available for the generation of an autologous vaccine. In addition, because they are allogeneic, the cells used in our vaccine are assured of being destroyed without genetic transfer, thus preventing the undesirable transfer of genetic material to host cells.

Thus, we have provided the art with a renewable, safe, cost-effective, and potent technique for delivering antigens specific to tumors or to infectious agents to the immune system of a mammal. The allogeneic cellular vaccine stimulates an effective immune response directed against these antigens even in immunologically privileged compartments.

The following examples are provided for exemplification purposes only and are not intended to limit the scope of the invention described above.

EXAMPLE 1

This example demonstrates the construction of cell lines expressing EGFRvIII.

The majority of high grade malignant gliomas, which are the most common histologic subtype of brain tumor and have the worst clinical outcome (Davis et al. 1995), express both wild type and an episomal mutant form of the epidermal growth factor receptor. The most frequently detected EGFR mutant, called EGFR variant III (EGFRvIII), is characterized by an in-frame deletion resulting in loss of 267 amino acids spanning the first and second extracellular domains of the receptor, with substitution of a glycine residue at the novel splice site (Merlino et al. 1985; Wong et al. 1987; Humphrey et al. 1988; Batra et al. 1994; Kurpad et al. 1995). The expression of cell surface EGFRvIII is immunologically detectable, and this tumor-associated antigen provides an excellent model for the examination of target-specific immune therapy for CNS tumors.

The B16-F10 cell line (B16) derived from a spontaneous melanoma in a C57BL/6J mouse (H-$2^q$) was generously provided by I. Fidler (M. D. Anderson Cancer Center, Houston, Tex.) (Fidler 1975). The murine pre B cell line 300.19 derived from Abelson murine leukemia virus-transformed bone marrow cells in an NIH/Swiss mouse (H-$2^q$) was kindly provided by T. Tedder (Duke University Medical Center, Durham, N.C.) (Alt et al. 1981). NR6 is a 3T3 fibroblast line derived in a NIH/Swiss mouse (H-$2^q$). The 560 cell line was derived from an intracerebral transplant of a spontaneous astrocytoma from a VM/Dk mouse (H-$2^b$) (Serano et al. 1980). The use of the 300.19 allogeneic cell line for the production of humoral responses to specific proteins was described by Tedder et al. 1990 and Spertini et al. 1991. The 300.19 cell line was grown in RPMI-1640 media (Life Technologies, Inc., Grand Island, N.Y.) containing 5% (vol/vol) fetal calf serum. All other cell lines were grown in zinc option medium (Life Technologies, Grand Island, N.Y.) containing 5% (vol/vol) fetal calf serum. All cell lines were shown to be free from Mycoplasma contamination as previously described (Kurtzberg and Hershfield 1985). All experiments used 6-to 12-week-old female C57BL/6J mice (The Jackson Laboratory, Bar Harbor, Me.), which were maintained in a virus-free environment in accordance with the Laboratory Animal Resources Commission standards.

The murine cell lines NR6, 300.19, B16 and 560 were stably transfected with the pHbAPr-1-neo vector containing the full length cDNA for EGFRvIII or with vector alone using previously described methods (Batra et al. 1995). G418 selection was used to derive cells with integrated copies of transfected DNA. G418 resistant clones were screened for expression of EGFR mutant protein by indirect immunofluorescence and flow cytometry.

Flow cytometry analysis was performed using a FACSort (Becton-Dickinson). The laser was tuned at 488 nm with an output power of 200 mW. During analysis the fluorescence signal was collected via a dichroic mirror (<560 nm pass) and a DF530/30 nm band pass filter. For analysis of receptor number, positivity was defined by comparing the fluorescence of labeled cells with that of isotype labeled controls. The mean fluorescence of cells was determined directly from single parameter histograms.

Stable clones successfully transfected with the EGFRvIII were designated "M" i.e.: B16M, NR6M, 300.19M and 560M, or "V" for vector only i.e.: B16V and 300.19V. The number of EGFRvIII binding sites per cell was quantitated by staining specifically with the L8A4-FITC labeled antibody followed by analysis with the Quantum simply cellular microbeads and software (Flow Cytometry Standards Co. San Juan PR.) (Lopez et al. 1992). Parallel studies using $^{131}$I labeled MAb and Scatchard analysis gave similar results (not shown).

FIGS. 1A through 1D compare the reactivity of the untransfected parent and the transfected cell lines used in these studies with L8A4 MAb specific for EGFRvIII. Estimated numbers of EGFRvIII molecules per cell for each transfected cell line as determined by quantitative flow cytometry using commercially available fluorescence calibration beads were: B16M $1\times10^5$, 300.19M $7\times10^4$, NR6M $5\times10^5$ and 560M $3\times10^5$.

EXAMPLE 2

This example demonstrates that immunization with allogeneic EGFRvIII bearing cells protects against tumor challenge with EGFRvIII bearing tumors within the CNS.

300.19, 300.19V or 300.19M cells were harvested, then washed twice in serum-containing medium and twice in Dulbecco's phosphate buffered saline (DPBS). Cell pellets were resuspended in DPBS at a concentration of $2\times10^7$ trypan blue-resistant cells/ml.

Groups of C57BL/6J mice received subcutaneous vaccination near the right groin in a volume of 500 µl with DPBS containing $1\times10^7$ 300.19 parent cells, $1\times10^7$ 300.19V cells or $1\times10^7$ 300.19M cells. The mice were then challenged in the brain one week later with either 200 viable untransfected B16 or the transfected B16M cells (FIG. 2A and Table 1A).

Immunization with either DPBS alone or 300.19M cells did not protect against CNS challenge with parental B16 cells, with all animals succumbing to tumor with a median survival 22 days. In addition, immunization with DPBS alone, untransfected 300.19 cells, or 300.19V cells transfected with only the pHbAPr-1-neo vector did not protect against CNS challenge with B16M cells, with all animals succumbing to tumor challenge. The median survival of animals undergoing tumor challenge with B16M cells was significantly prolonged to 36 days when compared to survival of animals undergoing tumor challenge with B16 parent cells, independent of the vaccination type given. This suggests that the EGFRvIII protein expressing B16M cells had a reduced rate of tumor growth when compared to the parent B16 cell line in these animals.

Vaccination of animals with 300.19M cells prior to challenge in the brain with B16M cells led to a significant improvement in median survival to 80+ days when compared to groups immunized with DPBS, 300.19 cells, or 300.19V cells and challenged with B16M cells or groups immunized with DPBS or 300.19 and challenged with parental B16 cells (FIG. 2A) ($p<0.02$ in all cases). In addition, 50% of animals in this group were alive with no evidence of tumor when the experiment was terminated at 80 days.

treatment groups were compared using the Wilcoxin log-rank test.

EXAMPLE 3

This example demonstrates that treatment with allogeneic-EGFRvIII bearing cells prolongs survival in mice with established EGFRvIII bearing tumors within the CNS.

In considering the future clinical application of such a vaccination strategy, a realistic model is to treat animals with tumor present at the time of vaccination. Thus, in the next experiments 200 B16M cells were implanted in the brain of unvaccinated mice, and these mice were treated 4 days later with either 300.19M cell vaccination or DPBS (FIG. 2B, Table 1B). Mice treated with the 300.19M vaccine had a 42% longer median survival, although there were no long term survivors.

These studies demonstrate that immunization with 300.19 cells transfected with EGFRvIII provides antigen-specific immunity against syngeneic EGFRvIII-bearing tumors in the CNS.

EXAMPLE 4

This example demonstrates the histologic characterization of immunization sites in response to 300.19M vaccination.

Animals receiving the live 300.19 cells as vaccines developed tumors at the site of immunization which measured a maximal diameter of 1–2 cm by 7–10 days and then spontaneously regressed by day 14. Histologic examination of immunization sites at day 7 showed a moderate inflammatory infiltrate in both 300.19 and 300.19M immunization

TABLE 1

Survival data of C57BL/J6 mice after various immunizations and tumor challenges

| | Immunization | Intracranial Tumor Challenge | | "P" Value |
|---|---|---|---|---|
| | | B16F10 Untransfected Survival Days median(range) | B16M Survival Days median(range)(n) | |
| | | A Protection Experiments | | |
| a) | 300.19M | | 80(37–80)(10) | |
| b) | DPBS | 22(21–24)(5) | | a vs b p < 0.0001 |
| c) | 300.19M | 21(21–26)(5) | | a vs c p < 0.0001 |
| d) | DPBS | | 36.50(26–44)(15) | a vs d p = 0.0002 |
| e) | 300.19 | | 37(26–44)(5) | a vs e p = 0.0029 |
| f) | 300.19V | | 36(20–42)(6) | a vs f p = 0.0022 |
| | | B Treatment of Established Tumor | | |
| a) | DPBS | | 26(20–40)(7) | |
| b) | 300.19M 4 days post tumor challenge | | 37(32–47)(7) | a vs b p = 0.0289 |
| | | C Lymphocyte Depletion Experiments | | |
| a) | 300.19M | | 49(37–80)(7) | |
| b) | 300.19M/CD4 depletion | | 41(33–46)(8) | a vs b p = 0.013 |
| c) | 300.19M/CD8 depletion | | 41(33–46)(7) | a vs c p = 0.0169 |
| d) | 300.19M/NK cell depletion | | 47.5(29–80)(6) | a vs d p = N.S. |

Immunizations and tumor challenges were performed with the various cell lines as described under materials and methods Survival estimates and median survivals were determined using the method of Kaplan and Meier. Survival data for .

sites. The majority of cells observed were viable 300.19/300.19M cells. The infiltrating lymphocyte population was composed almost entirely of T cells, with $CD8^+$ cells more frequently observed than $CD4^+$ cells. This lymphocytic infiltrate into the immunization site was more marked in the EGFRvIII bearing 300.19M tumors when compared to 300.19 parent tumors in each section examined, suggesting that the presence of the EGFRvIII protein may have contributed to host response.

EXAMPLE 5

This example demonstrates the histologic characterization of CNS tumors after 300.19M vaccination.

Tissues for immunohistochemistry were snap frozen in Tissue-Tek O.C.T. (Miles, Elkhart, Ind.), sectioned at 4 $\mu$m onto gelatin-coated slides and fixed in cold acetone. Immunoperoxidase staining was performed using the avidin-biotin-peroxidase complex method (Vector Labs, Burlingame, Calif.). Primary antibodies were GK 1.5 (CD4; Dialynas et al. 1983; obtained from the American Type Culture Collection), 53-6.72 (CD8), F4/80 (anti-macrophage; Walker 1987, obtained from the American Type Culture Collection), the polyclonal rabbit anti-asialo GM1 antibody (NK cells; obtained commercially from Wako Chemicals, Richmond, Va.) and L8A4 (anti-EGFRvIII Wikstrand et al. 1995). Secondary antibodies were biotinylated goat anti-rat immunoglobulin (Vector Laboratories) and goat anti-rabbit immunoglobulin (Southern Biotechnology Associates, Birmingham, Ala.). Isotype matched rat and polyclonal rabbit immunoglobulins were used as negative controls for monoclonal and polyclonal antibodies respectively. Sections were developed with 3,3'-diaminobenzidine tetrahydrochloride (Sigma), counterstained with 1% hematoxylin, and permanently mounted.

Figure 3B:
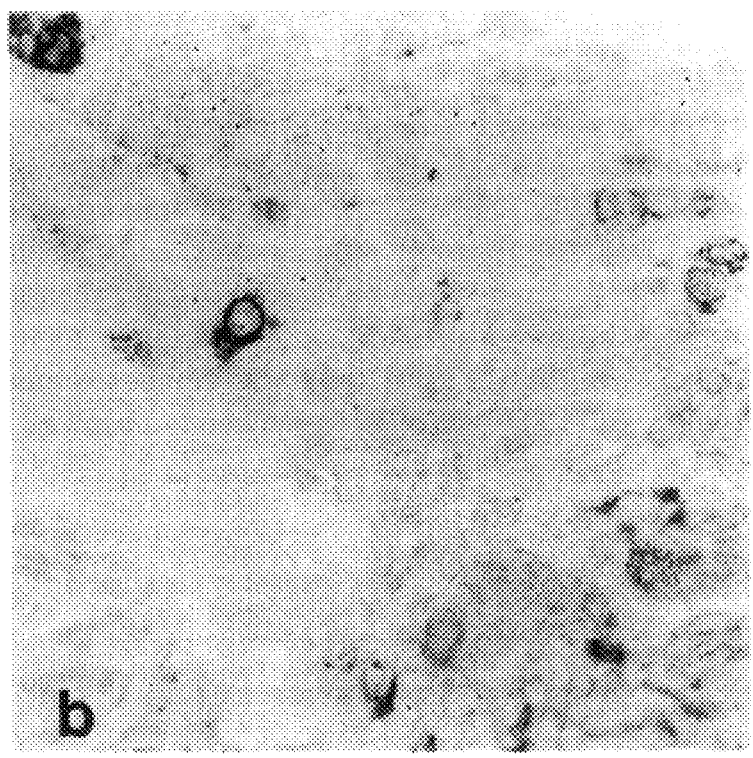
FIG. 3B shows CD4+ cells. Lymphocyte infiltrate was more marked in the 300.19M immunized animals as compared to DPBS immunized (not shown).

FIGS. 3A and 3B show immunohistochemical sections of CNS tumors from a 300.19M vaccinated animal.

A sparse inflammatory infiltrate was observed in tumors of both groups. The most frequent inflammatory cells identified were the F4/80 reactive macrophages present primarily in a peritumoral distribution surrounding the tumor foci. The infiltrating lymphocyte population was composed entirely of T cells, with $CD8^+$ cells more frequently observed than $CD4^+$ cells. Both $CD8^+$ and $CD4^+$ cellular infiltrates into the CNS tumor sites were more marked in the 300.19M immunized animals when compared to DPBS immunized animals in each section examined.

EXAMPLE 6

This example demonstrates that immunization with 300.19 cells transfected with EGFRvIII does not generate significant antibody production.

To determine if humoral immunity was generated by 300.19 vaccination and contributed to tumor rejection, immune sera from triplicate animals immunized with DPBS, 300.19, or 300.19M were collected and antibody titers against the NR6M EGFRvIII expressing cell line were determined by RIA as previously described (Wikstrand et al. 1993; Wikstrand et al. 1995). No significant reactivity with EGFRvIII could be detected in any of the serum samples tested (data not shown).

EXAMPLE 7

This example demonstrates that immunization with 300.19 cells transfected with EGFRvIII generates MHC restricted specific cytotoxic activity in vitro.

The rejection of allogeneic grafts is regarded as one example of a classical cellular immune response and is often of impressive magnitude (Billingham et al. 1954). Such rejection of foreign tissue involves both a direct and an indirect pathway. In the direct pathway, T-cell receptors directly recognize intact allogeneic major histocompatibility (MHC) molecules, with or without bound peptides on the surface of target cells. In the indirect pathway, T-ell receptors recognize MHC/allopeptide complexes after processing and presentation by self antigen presenting cells. Recognition by the T cell receptor leads to the activation of T helper cells which secrete cytokines and provide the necessary signals for the growth and maturation of the effector cytotoxic T lymphocytes (CTL), which mediate allogeneic cell rejection (Cuturi et al. 1994; Watschinger 1995).

In vitro cell-mediated cytotoxicity assays were performed using standard procedures (Coligan 1994). Briefly, whole spleens were removed from anesthetized mice, under sterile conditions, placed into sterile petri dishes, gently minced, and pressed through wire mesh. Splenocytes were collected, washed in RPMI-1640 media, and pelleted. The pellet was resuspended in a mixture of 0.15M $NH_4Cl$, 1.0 mM $KHCO_3$, and 0.1M $Na_2EDTA$ at pH 7.3, incubated at 37° C. for 1 minute to lyse red blood cells, then remaining cells were washed x2 with RPMI-1640. Cells were resuspended at a concentration of $1.5 \times 10^7$ viable cells/ml and restimulated in vitro for five days on monolayers of $1 \times 10^6$ irradiated (5,000 rads) and mitomycin C treated (80ug/ml) B16 M cells in 5 ml of Iscove Modified Dulbecco's media with 10% FCS, 100 IU/ml of penicillin, 100 mg/mL of streptomycin, and $5 \times 10^{-5}$ M mercaptoethanol. Viable effector cells were collected at the end of the five days by gradient centrifugation over Ficoll-Paque (Pharmacia LKB, Milwaukee, Wis.). Serial dilutions of effector cells were added to 96-well V-bottom plates (Falcon, Becton Dickinson Labware, Franklin Laes, N.J.) containing viable target cells that had been labeled with $^{51}$ chromium by a 1.25 hour incubation with $Na_2{}^{51}CrO_4$ at 37° C. and 5% $CO_2$. The plates were centrifuged at 200 g for 30 seconds and incubated at 37° C. and 5% $CO_2$ for 4 hours. Cell free supernatant was then harvested, and $^{51}Cr$ content determined. Maximal release was determined by adding Triton X-100 to target cells. Spontaneous release was determined from wells without effector cells. Percent lysis was calculated as follows:

% Lysis=experimental release–spontaneous release/maximal release–spontaneous releasex100

Figure 4A:
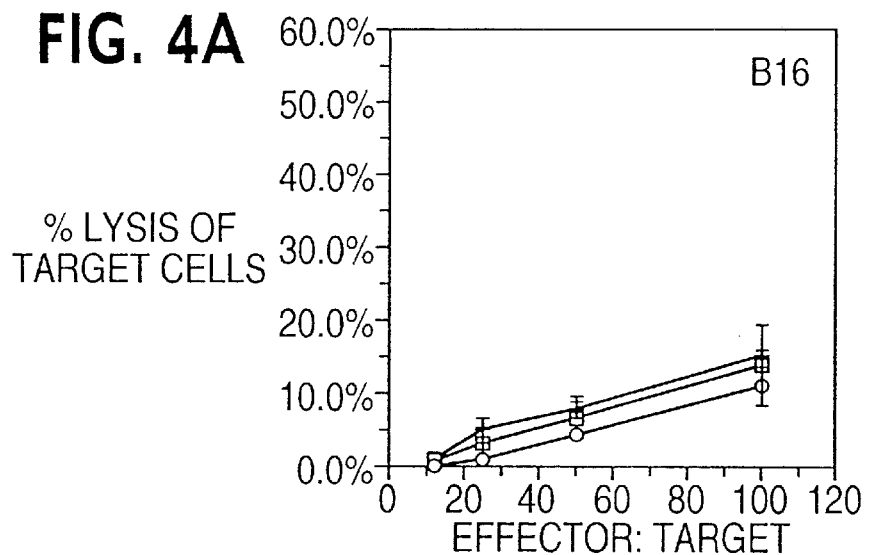
FIG. 4A shows cytotoxic activity measured by chromium release assay against the B16F10 parent.
Figure 4B:
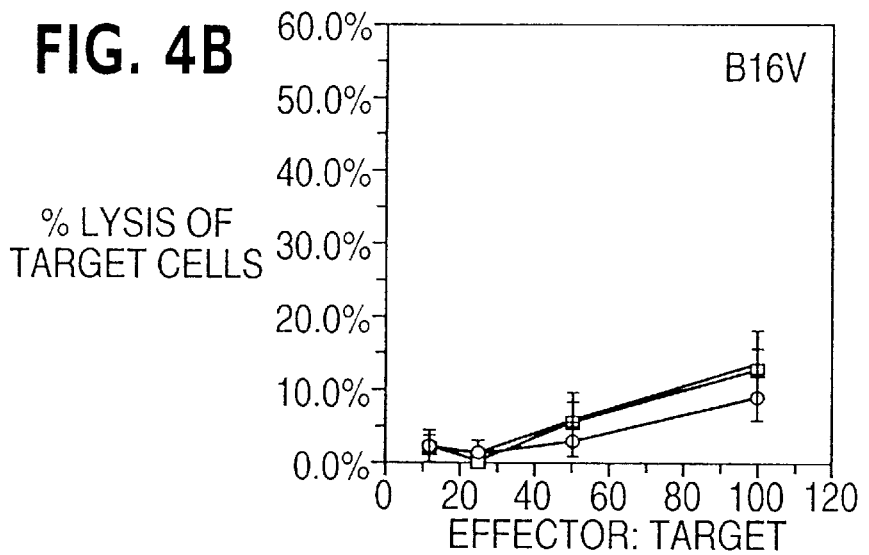
FIG. 4B shows cytotoxic activity measured by chromium release assay against B16V cells.
Figure 4C:
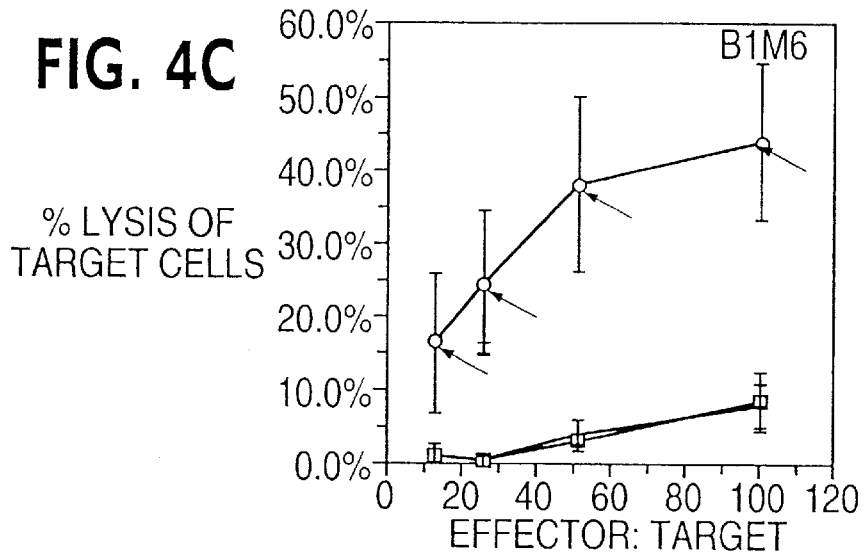
FIG. 4C shows cytotoxic activity measured by chromium release assay against B16M cells. In all figures arrows indicate points of significant differences in lysis ($p<0.05$). Error bars indicate one standard deviation of the mean of triplicate animals, each assays individually in triplicate.

The standard cytotoxicity assays described above were performed using splenocytes harvested from immunized animals seven days after immunization and restimulated for 5 days in vitro with B16M cells. Cytotoxic activity was then tested using three B16 lines as targets: B16 parent, B16V, and B16M. As shown in FIG. 4, this immunization strategy induced specific cytotoxic T lymphocyte (CTL) response to B16M. The B16 parent and B16V control cell lines were not lysed by the CTL demonstrating the specificity for the EGFRvIII antigen.

In a separate series of experiments to determine if this cytotoxic activity was MHC-restricted, splenocytes from immunized animals were tested for cytotoxic activity against B16M and two alternative EGFRvIII expressing cell lines. 560M is derived from the VM/Dk strain of mouse which although not syngeneic with the C57BL/6J strain, shares an H-$2^b$ MHC type. The NR6M line derived from NIH Swiss 3T3 cells has an H-2 $^q$ MHC type, as does the 300.19. As shown in FIG. 5A and C specific CTL responses were seen to both the H $2^b$ cell lines B16M and 560M. No statistically significant lysis of the H-$2^q$ expressing NR6M cells occurred FIG. 5B) despite expression of larger amounts of the EGFRvIII protein, thus confirming (H-$2^b$) MHC-restricted killing.

EXAMPLE 8

This example demonstrates the immune subsets involved in the response to immunization with 300.19 cells transfected with EGFRvIII.

In order to examine the role of anti tumor effector cells in vivo, naive C57BL/6J were immunized with 300.19M cells using the same protocol as described in Example 2. Ten days later mice were depleted of either CD8+, CD4+ or NK cells by in vivo administration of antibody or left with a complete T cell repertoire. GK1.5, 2.43 (Sarmiento et al. 1980, obtained from the American Type Culture Collection) and anti-asialo GM1 antibodies were used to deplete CD4+, CD8+, and natural killer (NK) cell subsets in vivo respectively using standard techniques (Coligan 1994). Vaccinated mice were injected once i.v. four days prior to tumor challenge and then i.p. every three days thereafter with pre-titrated amounts of one of these antibodies. In a cohort of mice that paralleled the experimental groups, flow cytometric analysis of splenocytes using fluorescein isothiocyanate-labeled, CD4 (H129.19) and CD8 (53-6.72) antibodies (Pharmingen, San Diego, Calif.), confirmed a >97% depletion of the targeted subset and normal levels of the other subsets both at the time of tumor challenge and again prior to the final antibody injection. Immunohistochemical staining of spleens from depleted mice in parallel groups or at the time of death from tumor confirmed depletion of the targeted subsets (CD4, CD8, or NK).

After depletion, mice were challenged with intracerebral B16M cells. Cells were harvested by trypsinization, washed twice in DPBS, mixed with an equal volume of 10% methylcellulose in zinc option medium and loaded into a 250 ml syringe (Hamilton, Reno, Nev.) with an attached 25-gauge needle. The tip of the needle was positioned at the bregma, 2 mm to the right of the cranial midline suture and 4 mm below the surface of the skull using a Kopf stereotactic frame (David Kopf Instruments, Tujunga, Calif.). 200 cells in a volume of 5 ml were then implanted into the right caudate nucleus of the brain of C57BL/6J mice. DPBS immunized mice were also challenged as a control (Table 1C). These studies revealed that both CD4+ and CD8+ cells were essential in mediating the prolonged survival in the 300.19M vaccinated animals. Survival estimates and median survivals were determined using the method of Kaplan and Meier (Kaplan and Meier 1958). Survival data was compared using the Wilcoxon log-rank test. Student's t test was used for calculating the significance of other data. Statistical significance was determined at the 0.05 level. No significant difference in median survivals could be demonstrated when comparing NK depleted animals and those with a complete T cell repertoire, suggesting that NK cells were not essential to this response.

Immunohistochemical examination was also performed on CNS tissues from representative animals after the specific lymphocyte depletion outlined above. This analysis confirmed the absence of the appropriate lymphocyte subset from the CNS after depletion. In addition, as we have observed in a previous study (Sampson et al. 1996), mice depleted of CD4+ cells maintained an infiltrate of CD8+ cells. In contrast, mice depleted of CD8+ cells failed to develop an infiltrate of CD4+ cells in the CNS tumors despite normal CD4+ cells in the spleen.

Finally, in order to evaluate the role of lymphocyte subsets in the cytolytic activity in vitro, splenocytes from immunized animals were tested for cytotoxicity against B16M in the presence of saturating concentrations of CD4, or CD8, or anti-asialo GM1 (NK) blocking monoclonal antibodies (FIG 5D). Blockade of CD8 function led to a significant reduction in cytotoxicity whereas no such reduction in cytotoxicity could be demonstrated for CD4. Blockade of NK function with the anti-asialo GM1 antibodies also led to significant reduction in cytotoxicity but only at the lower effector to target ratios.

Taken together these data suggest that the direct antitumor effect offered by immunization with 300.19 cells transfected with EGFRvIII is mediated predominantly by MHC class I-restricted cytotoxicity through the action of CD8+ lymphocytes. This effect in vivo is also dependent on the presence of adequate numbers of CD4+ cells.

REFERENCES

Alt, F., Rosenberg, N., Lewis, S., Thomas, E. and Baltimore, D. (1981). Organization and reorganization of immunoglobulin genes in A-MULV-transformed cells: rearrangement of heavy but not light chain genes. Cell 27: 381–90.

Aoki, T., Tasiro, K., Miyatake, H. I., Kinashi, T., Nakano, T., Oda, Y., Kikuchi, H. and Honjo, T. (1992). Expression of murine interleukin 7 in murine glioma cell line results in reduced tumorigenicity in vivo. Proceedings of the National Academy of Sciences USA 89: 1850–4.

Batra, S. K., Castelino-Prabhu, S., Wikstrand, C. J., Xiaopei, Z., Humphrey, P. A., Friedman, H. S. and Bigner, D. D. (1995). Epidermal growth factor ligand-independent, unregulated, cell-transforming potential of a naturally occurring human mutant EGFRvIII gene. Cell growth and diff. 6: 1251–1259.

Batra, S. K., Rasheed, B. K., Bigner, S. H. and Bigner, D. D. (1994). Oncogenes and anti-oncogenes in human central nervous system tumors. Lab Invest 71: 621–37.

Billingham, R. E., Brent, L. and Medawar, P. B. (1954). Quantitative studies on tissue transplantation immunity. II The origin strength and duration of actively and adoptively acquired immunity. Proc Roy Soc London B143: 58–80.

Coligan, J. E., Kruisbeek, A. M., Margulies, D. H., Shevach, E. M. & Strober, W. (1994). Current Protocols in Immunology. Greene and Wiley-Interscience, New York.

Cuturi, M. C., Blancho, G., Josien, R. and Soulillou, J. P. (1994). The biology of allograft rejection. Curr Opin Nephrol Hypertens 3: 578–84.

Dal Canto, M. C., Melvold, R. W., Kim, B. S. and Miller, S. D. (1995). Two models of multiple sclerosis: experimental allergic encephalomyelitis (EAE) and Theiler's murine encephalomyelitis virus (TMEV) infection. A pathological and immunological comparison. Microsc Res Tech 32: 215–29.

Davis, F. G., Malinski, N., Haenszel, W., Chang, J., Flannery, J., Gershman, S., Dibble, R. and Bigner, D. D. (1995). Primary brain tumor incidence rates in four United States regions, 1985–89: a pilot study. Neuroepidemiol 15:103–112.

Dialynas, D. P., Quan, Z. S., Wall, K. A., Pierres, A., Quintans, J., Loken, M. R., Pierres, M. and Fitch, F. W. (1983). Characterization of the murine T cell surface molecule, designated L3T4, identified by the monoclonal antibody GK1.5: Similarity of L3T4 to the human Leu 3/T4 molecule. J. Immunol 131: 2445–2451.

Dillman, R. O., Nayak, S. K. and Beutel, L. (1993). Establishing in vitro cultures of autologous tumor cells for use in active specific immunotherapy. J Immunother 14: 65–9.

Fakhrai, H., Dorigo, O., Shawler, D. L., Lin, H., Mercola, D., Black, K. L., Royston, I. and Sobol, R. E. (1996). Eradication of established intracranial rat gliomas by transforming growth factor b antisense gene therapy. Proc. Nat. Acad. Sci. USA 93: 2909–2914.

Fidler, I. J. (1975). Biological behavior of malignant melanoma cells correlated to their survival in vivo. Cancer Res 35: 218–224.

Glick, R. P., Lichtor, T., Kim, T. S., Ilangovan, S. and Cohen, E. P. (1995). Fibroblasts genetically engineered to secrete cytokines suppress tumor growth and induce antitumor immunity to a murine glioma in vivo. Neurosurgery 36: 548–55.

Grooms, G. A., Eilber, F. R. and Morton, D. L. (1977). Failure of adjuvant immunotherapy to prevent central nervous system metastases in malignant melanoma patients. J. Surg. Oncol. 9: 147–153.

Humphrey, P. A., Wong, A. J., Vogelstein, B., Friedman, H. S., Werner, M. H., Bigner, D. D. and Bigner, S. H. (1988). Amplification and expression of the epidermal growth factor receptor gene in human glioma xenografts. Cancer Res 48: 2231–8.

Kaplan, E. L. and Meier, P. (1958). Nonparametric estimation from incomplete observations. J. Am. Statist. Assoc. 53: 457–481.

Kurpad, S. N., Zhao, X. G., Wikstrand, C. J., Batra, S. K., McLendon, R. E. and Bigner, D. D. (1995). Tumor antigens in astrocytic gliomas. Glia 15: 244–56.

Kurtzberg, J. and Hershfield, M. S. (1985). Determinants of deoxyadenosine toxicity in hybrids between human T- and B-lymphoblasts as a model for the development of drug resistance in T-cell acute lymphoblastic leukemia. Cancer Res 45: 1579–1586.

Logan, T. F., Shannon, W., Bryant, J., Kane, P., Wolmark, N., Posner, M., Kirkwood, J. M., Ernstoff, M. S., Futrell, J. W., Straw, L. D. and et al. (1993). Preparation of viable tumour cell vaccine from human solid tumours: relationship between tumour mass and cell yield. The Tissue Bank, Pittsburgh Cancer Institute. Melanoma Res 3: 451–5.

Lopez, J. G., Chew, S. J., Thompson, H. W., Malter, J. S., Insler, M. S. and Beuerman, R. W. (1992). EGF cell surface receptor quantitation on ocular cells by an immunocytochemical flow cytometry technique. Invest Ophthalmol Vis Sci 33: 2053–62.

Medawar, P. B. (1948). Immunity to homologous grafted skin: III. The fate of skin homografts transplanted to the brain, to subcutaneous tissues, and to the anterior chamber of the eye. Br. J of Exp Path 29: 58–69.

Merlino, G. T., Ishii, S., Whang-Peng, J., Knutsen, T., Xu, Y. H., Clark, A. J., Stratton, R. H., Wilson, R. K., Ma, D. P., Roe, B. A. and et al. (1985).

Structure and localization of genes encoding aberrant and normal epidermal growth factor receptor RNAs from A431 human carcinoma cells. Mol Cell Biol 5: 1722–34.

Mitchell, M. S. (1989). Relapse in the central nervous system in melanoma patients successfully treated with biomodulators. J. Clin. Oncol 7: 1701–1709.

Mitchell, M. S., Harel, W., Kan-Mitchell, J., LeMay, L. G., Goedegebuure, P., Huang, X. Q., Hofman, F. and Groshen, S. (1993). Active specific immunotherapy of melanoma with allogeneic cell lysates. Rationale, results, and possible mechanisms of action. Ann N Y Acad Sci 690: 153–66.

Mizuno, M., Yoshida, J., Takaoka, T. and Sugita, K. (1994). Liposomal transfection of human g-interferon gene into human glioma cells and adoptive immunotherapy using lymphokine-activated killer cells. J. Neurosurg 80: 510–4.

Murphy, J. B. and Sturm, E. (1923). Conditions determining transplantability of tissues in the brain. J Exp Med 38: 183–97.

Ridley, A. and Cavanagh, J. B. (1971). Lymphocytic infiltration in gliomas: Evidence of possible host resistance. Brain 94: 117–124.

Sampson, J. H., Archer, G. E., Ashley, D. M., Hale, L. P., Dranoff, G. and Bigner, D. D. (1996). Subcutaneous vaccination with irradiated, cytokine-producing tumor cells stimulates CD8+ cell mediated immunity against tumors located in the "immunologically privileged central nervous system. Proc Natl Acad Sci U S A 93: 10399–10404.

Sarmiento, M., Glasebrook, A. L. and Fitch, F. W. (1980). IgG or IgM monoclonal antibodies reactive with different determinants on the molecular complex bearing Lyt 2 antigen block T cell-mediated cytoloysis in the absence of complement. J. Immunol 125: 2665–2672.

Scheinberg, L. C., Levy, A. and Edelman, F. (1965). Is the brain an limmunologically privileged site¡?2. Studies in induced host resistance to transplantable mouse glioma following irradiation of prior implants. Arch. Neurol 13: 283–286.

Scheinberg, L. C., Suzuki, K., Edelman, F. and Davidoff, L. M. (1963). Studies in immunization against a transplantable cerebral mouse glioma. J. Neurosurg 20: 312–317.

Serano, R. D., Pegram, C. N. and Bigner, D. D. (1980). Tumorigenic cell culture lines from a spontaneous VM/Dk murine astrocytoma (SMA). Acta Neuropathol. 51: 53–64.

Shirai, Y. (1921). Transplantations of rat sarcomas in adult heterogeneous animals. Japanese Medical World 1: 14–15.

Spertini, O., Kansas, G. S., Reimann, K. A., Mackay, C. R. and Tedder, T. F. (1991). Function and evolutionary conservation of distinct epitopes on the leukocyte adhesion molecule-1 (TQ-1, Leu-8) that regulate leukocyte migration. J Immunol 147: 942–9.

Strauss, M. M., Bigner, S. H. and Bigner, D. D. (1982). Experimental allergic encephalomyelitis in Lewis rats bearing avian sarcoma virus-induced brain tumors. J Neuroimmunol 2: 283–94.

Swanborg, R. H. (1995). Experimental autoimmune encephalomyelitis in rodents as a model for human demyelinating disease. Clin Immunol Immunopathol 77: 4–13.

Takaoka, T., Yoshida, J., Mizuno, M. and Sugita, K. (1994). Transfection-induced tumor necrosis factor-a increases the susceptibility of human glioma cells to lysis by lymphokine-activated killer cells: continuous expression of intercellular adhesion molecule-1 on the glioma cells. Japanese Journal of Cancer Research 85: 750–5 5.

Takeuchi, J. and Bamard, R. O. (1976). Perivascular lymphocytic cuffing in astrocytomas. Acta Neuropathol. (Berl.) 35: 265–271.

Tedder, T. F., Penta, A. C., Levine, H. B. and Freedman, A. S. (1990). Expression of the human leukocyte adhesion molecule, LAM1. Identity with the TQ1 and Leu-8 differentiation antigens. J Immunol 144: 532–40.

Tjuvajev, J., Gansbacher, B., Desai, R., Beattie, B., Kaplitt, M., Matei, C., Koutcher, J., Gilboa, E. and Blasberg, R. (1995). RG-2 glioma growth attenuation and severe brain edema caused by local production of interleukin-2 and interferon-gamma. Cancer Res 55: 1902–10.

Walker, W. S. (1987). Origins of macrophage diversity: Functional and phenotypic analysis of cloned populations of mouse splenic macrophages. Cell. Immunol. 107: 417–432.

Watanabe, Y., Kuribayashi, K., Miyatake, S., Nishihara, K., Nakayama, E., Taniyama, T. and Sakata, T. (1989). Exogenous expression of mouse interferon gamma cDNA in mouse neuroblastoma C1300 cells results in reduced tumorgenicity by augmented anti-tumor immunity. Proc. Natl. Acad. Sci. U.S.A. 86: 9456–9460.

Watschinger, B. (1995). How T cells recognize alloantigen: evidence for two pathways of allorecognition. Nephrol Dial Transplant 10: 1556–8.

Wikstrand, C. J., Hale, L. P., Batra, S. K., Hill, M. L., Humphrey, P. A., Kurpad, S. N., McLendon, R. E., Moscatello, D., Pegram, C. N., Reist, C. J. and al., e. (1995). Monoclonal antibodies against EGFRvIII are tumor specific and react with breast and lung carcinomas and malignant gliomas. Cancer Res 55: 3140–8.

Wikstrand, C. J., Stanley, S. D., Humphrey, P. A., Pegram, C. N., Archer, G. E., Kurpad, S., Shibuya, M. and Bigner, D. D. (1993). Investigation of a synthetic peptide as immunogen for a variant epidermal growth factor receptor associated with gliomas. J Neuroimmunol 46: 165–73.

Wong, A. J., Bigner, S. H., Bigner, D. D., Kinzler, K. W., Hamilton, S. R. and Vogelstein, B. (1987). Increased expression of the epidermal growth factor receptor gene in malignant gliomas is invariably associated with gene amplification. Proc Natl Acad Sci U S A 84: 6899–903.

Wood, G. W. and Morantz, R. A. (1979). Immunohistologic evaluation of the lymphoreticular infiltrate of human central nervous system tumors. J. Natl. Cancer Inst. 62: 485–491.

Yu, J. S., Wei, M. S., Chiocca, E. A., Martuza, R. L. and Tepper, R. I. (1993). Treatment of glioma by engineered interleukin 4-secreting cells. Cancer Res. 53: 3125–3128.

What is claimed is:

1. A method of immunizing a mammal against a tumor-associated antigen comprising the step of:
    immunizing the mammal with an allogeneic cell which has been transfected with a recombinant nucleic acid molecule which encodes a tumor-associated antigen, wherein the mammal mounts a cytotoxic immune response against the tumor-associated antigen, wherein the allogeneic cell expresses the tumor-associated antigen, and wherein the allogeneic cell does not express a syngeneic MHC determinant of the mammal.

2. The method of claim 1 wherein the tumor associated antigen is EGFRvIII.

3. The method of claim 1 wherein the tumor associated antigen is a melanoma-specific antigen.

4. The method of claim 1 wherein the tumor-associated antigen is a component of a central nervous system tumor.

5. A method of immunizing a mammal against two or more antigens comprising the step of:
    immunizing the mammal with an allogeneic cell which has been transfected with a recombinant nucleic acid comprising two or more open reading frames which encode antigens, wherein at least one of the open reading frames encodes a tumor-associated antigen, wherein the mammal mounts a cytotoxic immune response against the tumor-associated antigen, wherein the allogeneic cell expresses the antigens, and wherein the allogeneic cell does not express a syngeneic MHC determinant of the mammal.

6. The method of claim 5 wherein at least one of the antigens is a melanoma-specific antigen.

7. The method of claim 5 wherein at least one of the antigens is a component of a central nervous system tumor.

8. The method of claim 5 wherein the tumor-associated antigen is EGFRvIII.

9. A method of immunizing a mammal against a tumor-associated antigen comprising the steps of:
    determining the presence of a tumor-associated antigen in a mammal, wherein the mammal mounts an immune response against the tumor-associated antigen; and
    immunizing the mammal with an allogeneic cell which has been transfected with a recombinant nucleic acid molecule which encodes the tumor-associated antigen, wherein the allogeneic cell expresses the tumor-associated antigen, wherein the allogeneic cell does not express a syngeneic MHC determinant of the mammal, whereby the mammal mounts a cytotoxic immune response to the tumor-associated antigen.

10. The method of claim 9 wherein the tumor associated antigen is EGFRvIII.

11. The method of claim 1 wherein the tumor-associated antigen is a tumor-specific antigen.

12. The method of claim 5 wherein the tumor-associated antigen is a tumor-specific antigen.

13. The method of claim 9 wherein the tumor-associated antigen is a tumor-specific antigen.

* * * * *